United States Patent
Dalkidis et al.

(10) Patent No.: US 6,756,015 B2
(45) Date of Patent: Jun. 29, 2004

(54) APPARATUS FOR TREATING OBJECTS

(75) Inventors: Charilaos Dalkidis, Schwetzingen (DE); Stefan Kuenkel, Karlsruhe (DE); Ralf Eckert, Dossenheim (DE); Stefan Thiem, Heidelberg (DE)

(73) Assignee: Leica Microsystems Nussloch GmbH, Nussloch (DE)

(*) Notice: Subject to any disclaimer, the term of this patent is extended or adjusted under 35 U.S.C. 154(b) by 217 days.

(21) Appl. No.: 09/931,138

(22) Filed: Aug. 16, 2001

(65) Prior Publication Data

US 2002/0025276 A1 Feb. 28, 2002

(30) Foreign Application Priority Data

Aug. 22, 2000 (DE) .......................................... 100 41 227

(51) Int. Cl.[7] .......................... G01N 15/06; G01N 35/00; B01L 3/00; B05D 3/00; B05C 3/00
(52) U.S. Cl. .................... 422/68.1; 422/99; 422/104; 422/102; 436/46; 427/2.11; 118/423
(58) Field of Search .................. 422/63–65, 68.1, 422/104, 99, 102; 436/46; 118/423, 425; 427/2.11

(56) References Cited

U.S. PATENT DOCUMENTS

| | | | | |
|---|---|---|---|---|
| 3,976,028 A | * | 8/1976 | Howells et al. | 118/702 |
| 4,092,952 A | * | 6/1978 | Wilkie et al. | 118/58 |
| 4,353,856 A | * | 10/1982 | Muck et al. | 264/240 |
| 4,651,671 A | * | 3/1987 | Pedersen | 118/57 |
| 4,911,098 A | * | 3/1990 | Tabata | 118/423 |
| 5,573,727 A | * | 11/1996 | Keefe | 422/63 |
| 5,895,628 A | | 4/1999 | Heid et al. | 422/65 |
| 6,017,495 A | * | 1/2000 | Ljungmann | 422/65 |
| 6,180,061 B1 | * | 1/2001 | Bogen et al. | 422/64 |
| 6,183,693 B1 | * | 2/2001 | Bogen et al. | 422/64 |
| 6,258,322 B1 | * | 7/2001 | Meikle | 422/63 |
| 6,296,809 B1 | * | 10/2001 | Richards et al. | 422/64 |
| 6,387,326 B1 | * | 5/2002 | Edwards et al. | 422/63 |
| 6,436,348 B1 | * | 8/2002 | Ljungmann et al. | 422/63 |

\* cited by examiner

Primary Examiner—Jill Warden
Assistant Examiner—B. R. Gordon
(74) Attorney, Agent, or Firm—Hodgson Russ LLP

(57) ABSTRACT

An apparatus for treating objects, in particular cytological or histological specimens, having multiple processing stations and preferably a transport device for delivering the objects into and out of the processing stations, is characterized in that at least one heatable reagent station (1) is provided as a processing station.

6 Claims, 2 Drawing Sheets

APPARATUS FOR TREATING OBJECTS

CROSS REFERENCE TO RELATED APPLICATIONS

This invention claims priority of the German patent application 100 41 227.0 filed Aug. 22, 2000 which is incorporated by reference herein.

FIELD OF THE INVENTION

The invention concerns an apparatus for treating objects, in particular cytological or histological specimens, having multiple processing stations and preferably a transport device for delivering the objects into and out of the processing stations.

BACKGROUND OF THE INVENTION

The reader is referred, purely by way of example, to EP 0 849 582 A2. This document discloses a generic apparatus for treating objects, in particular cytological or histological specimens. In this, cytological or histological specimens are conveyed by way of an object carrier or basket to an automatic stainer, the automatic stainer comprising multiple processing stations.

The generic apparatus known from EP 0 849 582 A2 comprises various processing stations that are to be understood, however, as conventional reagent baths. No provision is made therein for more extensive measures to promote the action of the reagents or indeed to promote a reactive process.

SUMMARY OF THE INVENTION

It is the object of the present invention to configure and further develop an apparatus for treating objects, in particular cytological or histological specimens, in such a way that staining operations, actions of reagents, or indeed reactive processes can be promoted.

The aforesaid object is achieved by an apparatus characterized in that at least one heatable reagent station is provided as a processing station.

What has been recognized according to the present invention is that the action of reagents, for example the staining of tissue samples but also reactive processes, can be promoted by the fact that the reagent station is of heatable configuration. It is not necessary in this context to heat all the processing stations or indeed equip them with individual heating devices. The provision of a single heatable reagent station or a definable number of heatable reagent stations is sufficient, so that a "special treatment" can take place within that reagent station.

Advantageously, the reagent station could be provided as an additional processing station, in which case an arrangement, for example, in front of, alongside, or behind the actual processing station is then necessary or possible. A relevant clearance would need to be maintained.

It is also conceivable, however, to provide the reagent station as replacement for a conventional processing station, so that the heatable reagent station can easily be retrofitted. The electrical connection for the heating device could be introduced from outside the housing of the apparatus, so that no further installation effort is necessary. It is also conceivable to provide an electrical connection directly on the housing, a permanent electrical connection or wiring from the housing to the heatable reagent station then being necessary.

In particular to achieve sufficient flexibility for the apparatus, it is advantageous if in total two reagent stations, preferably arranged next to or behind one another, are provided. The provision of further heatable reagent stations is conceivable, in which context the actual number of reagent stations under discussion here should be adapted to the actual requirement.

Concretely, the reagent station could comprise a container that has dimensions similar to those of the containers of a conventional processing station. Simple replacement is thus possible, in which context heating and power supply must be ensured.

The container or the wall of the container could be produced from a thermally insulating material, specifically in order to prevent excessively rapid outward dissipation of heat. The heating device could be arranged inside the container (similarly to a heating element) or could be integrated into the wall or the floor of the container. The wall of the container could be produced from plastic or ceramic.

As an alternative to the embodiment recited above, the container could be produced from a thermally conductive material so that heat transfer inward—toward the liquid—is promoted. In this respect the container could be produced from metal. To decrease thermal radiation outward, the wall of the container could be surrounded by a thermal insulator so that the container operates similarly to a THERMOS® vessel.

In particularly advantageous fashion, the container has a highly thermally conductive and preferably heat-storing base, said base possibly being embodied as the bottom of the metal block forming the container. The heat-storing property of the container would thereby be promoted.

It has already been mentioned earlier that an electrical heating device, for example a heating element, could be integrated inside the container. It is also conceivable, however, to integrate the heating device into the base embodied as a metal block, so that the heat is transferred from there, by direct heat exchange, to the liquid or to the reagents. A corresponding electrical connection would need to be provided on the container, a plug connection being very particularly suitable in this context.

In additionally advantageous fashion, the reagent station could have a preferably thermally insulating holder for reception of the container. A recess for emplacement or insertion of the container could be configured inside the holder. In additionally advantageous fashion, the holder could comprise an electrical heating device that, in the context of a preferred embodiment, can be embodied as an electrical heating plate integrated into the holder. The holder would correspondingly need to possess electrical connections that in turn can be implemented in the form of plug connections.

The holder—with or without heating device—could be configured for simultaneous reception of two or more containers, the holder having for that purpose recesses in accordance with the number of vessels to be received. It is possible in this context for all the vessels emplaced into the holder to be heated simultaneously by a single heating device. To obtain the greatest possible flexibility for the apparatus claimed, the holder could comprise two or more heating devices operating independently of one another so that the individual vessels are heatable separately, in which context, if only one container is loaded, heating of only that container is also necessary and achievable. Energy consumption is thereby undoubtedly reduced.

In particular to prevent any overflow of the container into the housing and to prevent any undesired contamination with the reagents being used, the reagent station, in particular the holder serving to receive the container, is positioned in a pan, the pan possibly being inserted into the housing in place of the other processing stations (to replace one or two processing stations). In any event, the pan could comprise particular holding means for receiving and optionally securing the holder, in which in turn the container or containers are inserted. For connection of the electrical heating device, the pan could comprise electrical connections so that a direct electrical connection is possible without additional modification.

The pan could furthermore have an outflow, preferably in the form of an outflow fitting connectable to an outflow line, so that overflowed or dumped reagents can be discharged. A detector arranged in the pan could detect the fill level of the pan and trigger an alarm when a definable (critical) fill level in the pan is reached.

Lastly, be it noted that the heating device itself, or the heating plate, the holder, or even the pan, can be equipped with one or more temperature sensors so that closed-loop control is possible in consideration of adjustable temperature values. In this respect it is also possible to provide a temperature sensor inside the container so that closed-loop control of the liquid temperature present in the container can be performed. An integrated or separate control unit could be provided for closed-loop or open-loop control of the heating device. Retrofitting of the apparatus with a corresponding control unit is possible, external mounting being conceivable for simple retrofitting.

BRIEF DESCRIPTION OF THE DRAWINGS

There are various ways of advantageously embodying and developing the teaching of the present invention. The reader is referred, for that purpose, to the explanation below of an exemplary embodiment of the invention with reference to the drawings. In conjunction with the explanation of a preferred exemplary embodiment of the invention with reference to the drawings, an explanation is also given of generally preferred embodiments and developments of the teaching. In the drawings.

DETAILED DESCRIPTION OF THE INVENTION

Figure 1:
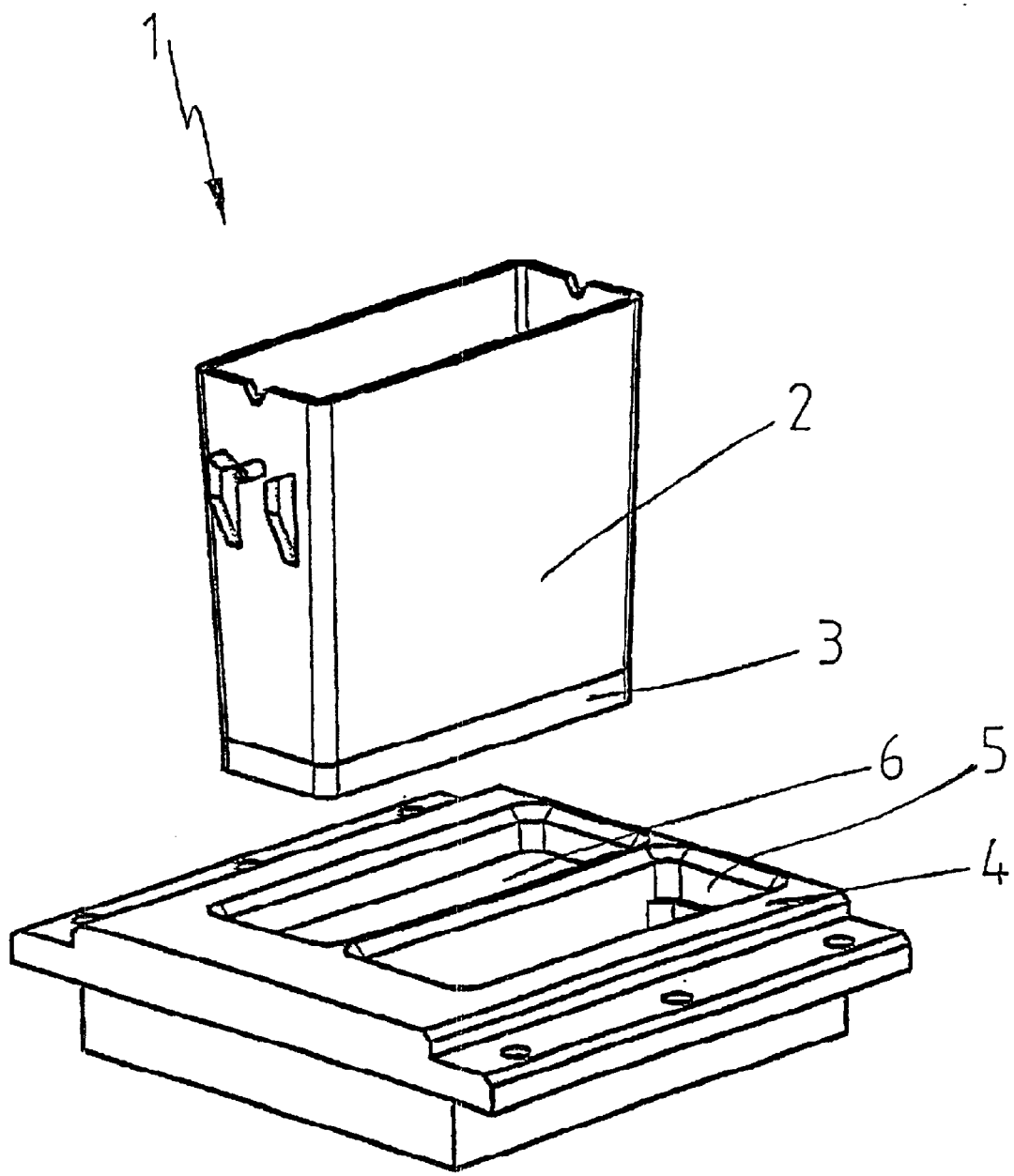
FIG. 1 shows, in a schematic view, an exemplary embodiment of a heatable reagent station for an apparatus according to the present invention, in particular for use in an automatic stainer.
Figure 2:
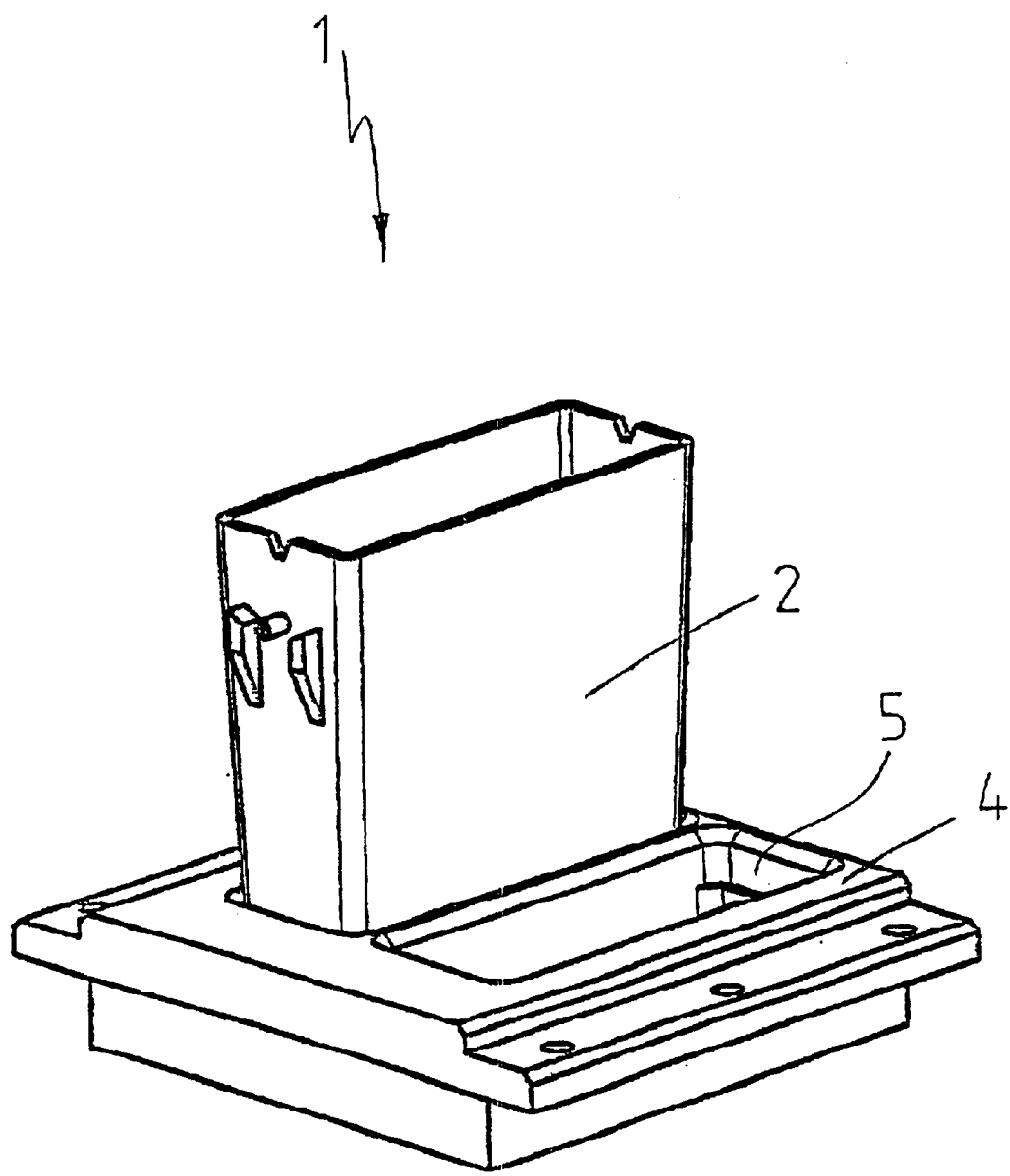
FIG. 2 shows the subject matter of FIG. 1 with a container inserted.

FIGS. 1 and 2 together show a heatable reagent station that is usable as a processing station in an apparatus according to the present invention or in an automatic stainer.

In the exemplary embodiment selected here, reagent station 1 is provided for replacement of a conventional processing station, in which context reagent station 1 can comprise containers 2. If two containers 2 are used simultaneously in the context of the exemplary embodiment selected here, they are arranged next to one another.

Container 2 is similar in its dimensions to the container of a conventional processing station, so that simple replacement is possible, especially in terms of space requirements.

In the exemplary embodiment selected here, container 2 is produced from a thermally conductive material, more precisely from metal. In the bottom region, container 2 has a highly thermally conductive and heat-storing base 3 that is embodied as a metal block. Base 3 is equipped on the underside with a flat surface, thus making possible planar contact upon a flat support.

The two Figures furthermore show that reagent station 1 has a holder 4 for the reception of container 2. Holder 4 is produced from a thermally insulating material, so that in the lower region of container 2, in particular in the region of base 3, heat dissipation outward is very considerably reduced.

Holder 4 has a total of two recesses 5 for the emplacement or insertion of two containers 2, only one container 2 being depicted in the Figures.

Container 2 furthermore comprises an electrical heating device that is integrated into holder 4 as electrical heating plate 6. Electrical connections are provided but are not shown in the Figures.

What is essential in the case of the concrete embodiment selected here is that container 2 comes into planar contact, with its base 3 of flat configuration, in planar fashion against heating plate 6 that is also flat in configuration, so that optimum heat transfer from electrical heating plate 6 to base 3 of container 2 is possible.

In conclusion, be it noted very particularly that the exemplary embodiment discussed above serves for discussion of the teaching claimed, but does not limit it to the exemplary embodiment.

Parts List

1 Heatable reagent station
2 Container
3 Base (of container), metal block
4 Holder (for container)
5 Recess (in holder)
6 Electrical heating plate (in holder)

What is claimed is:

1. In an apparatus for treating cytological or histological specimens of a type having a plurality of conventional processing stations and a transport device for delivering said specimens into and out of said plurality of processing stations, the improvement comprising:
at least one heatable reagent station being provided ms a processing station, said reagent station comprising a container having dimensions similar to those of a container of a conventional processing station and a thermally insulating holder for receiving said container, wherein said holder includes a recess in which said container is inserted and an electrical heating plate integrated into said holder.

2. In an apparatus for treating cytological or histological specimens of a type having a plurality of conventional processing stations and a transport device for delivering said specimens into and out of said plurality of processing stations, the improvement comprising:
at least one heatable reagent station being provided as a processing station, said reagent station comprising a container having dimensions similar to those of a container of a conventional processing station and a thermally insulating holder for receiving said container, wherein said holder is configured for receiving two or more said containers.

3. The improvement as defined in claim 2, wherein said holder comprises two or more heating devices operating independently of one another.

4. In an apparatus for treating cytological or histological specimens of a type having a plurality of conventional processing stations and a transport device for delivering said specimens into and out of said plurality of processing stations, the improvement comprising:

at least one heatable reagent station being provided as a processing station, said reagent station comprising a container having dimensions similar to those of a container of a conventional processing station, a thermally insulating holder for receiving said container, and a pan in which said holder is positioned, wherein said holder comprises an electrical heating device and said pan comprises electrical connections for collection of said heating device to a power supply.

5. In an apparatus for treating cytological or histological specimens of a type having a plurality of conventional processing stations and a transport device for delivering said specimens into and out of said plurality of processing stations, the improvement comprising:

at least one heatable reagent station being provided as a processing station, said reagent station comprising a container having dimensions similar to those of a container of a conventional processing station, a thermally insulating holder for receiving said container, and a pan in which said holder is positioned, wherein said pan has an outflow fitting connectable to an outflow line.

6. A heatable reagent station for use as a processing station for treating cytological or histological specimens, said reagent station comprising:

a container having a thermally conductive base;

an electrical heating plate operatively connected to said base; and a holder having a recess for receiving said container, said electrical heating plate being provided as part of said holder to contact said base when said container is inserted in said recess;

wherein said base includes a planar surface in contact with said heating plate.

* * * * *